(12) United States Patent
Gronfors et al.

(10) Patent No.: US 12,281,032 B2
(45) Date of Patent: Apr. 22, 2025

(54) METHOD OF EVALUATING AND OPTIONALLY SELECTING A SUITABLE CHEMISTRY FOR REMOVAL OF MICROPLASTICS IN A LIQUID MATRIX

(71) Applicant: KEMIRA OYJ, Helsinki (FI)

(72) Inventors: Outi Gronfors, Espoo (FI); Mehrdad Hesampour, Espoo (FI); Katriina Rajala, Espoo (FI); Lenita Lindberg, Espoo (FI)

(73) Assignee: KEMIRA OYJ, Helsinki (FI)

( * ) Notice: Subject to any disclaimer, the term of this patent is extended or adjusted under 35 U.S.C. 154(b) by 791 days.

(21) Appl. No.: 17/430,750

(22) PCT Filed: Feb. 18, 2020

(86) PCT No.: PCT/EP2020/054217
§ 371 (c)(1),
(2) Date: Aug. 13, 2021

(87) PCT Pub. No.: WO2020/169591
PCT Pub. Date: Aug. 27, 2020

(65) Prior Publication Data
US 2022/0135451 A1 May 5, 2022

(30) Foreign Application Priority Data
Feb. 18, 2019 (SE) .................................... 1950203-8
May 6, 2019 (SE) .................................... 4950532-0

(51) Int. Cl.
*C02F 1/52* (2023.01)
*C02F 1/00* (2023.01)
(Continued)

(52) U.S. Cl.
CPC ............ *C02F 1/5209* (2013.01); *C02F 1/001* (2013.01); *C02F 1/24* (2013.01); *C02F 1/5245* (2013.01); *C02F 1/56* (2013.01); *G01N 15/0211* (2013.01); *G01N 33/18* (2013.01); *C02F 2001/007* (2013.01); *C02F 2101/32* (2013.01);
(Continued)

(58) Field of Classification Search
CPC .......... C02F 1/5209; C02F 1/001; C02F 1/24; C02F 1/5245; C02F 1/56; C02F 2001/007; C02F 2101/32; C02F 2103/007; C02F 2209/003; C02F 2209/105; C02F 1/52;
(Continued)

(56) References Cited

FOREIGN PATENT DOCUMENTS

WO 2017168054 10/2017

OTHER PUBLICATIONS

Baiwen, Characteristics of microplastic removal via coagulation and ultrafiltration during drinking water treatment, 2018 (Year: 2018).*
(Continued)

*Primary Examiner* — Waqaas Ali
(74) *Attorney, Agent, or Firm* — Robin L. Teskin; Baker, Donelson, Bearman, Caldwell & Berkowitz PC

(57) ABSTRACT

The present invention relates to a method of evaluating and optionally selecting a suitable chemistry for removal of microplastics in a liquid matrix, said method comprising using at least one coagulant and/or flocculant and measuring fluorescence intensity and light scattering intensity of any particles in a sample volume of clarified liquid matrix by an optical measurement.

19 Claims, 3 Drawing Sheets

(51) Int. Cl.
    *C02F 1/24*     (2023.01)
    *C02F 1/56*     (2023.01)
    *G01N 15/0205*     (2024.01)
    *G01N 33/18*     (2006.01)
    *C02F 101/32*     (2006.01)
    *C02F 103/00*     (2006.01)
    *G01N 15/00*     (2006.01)

(52) U.S. Cl.
    CPC .. *C02F 2103/007* (2013.01); *C02F 2209/003* (2013.01); *C02F 2209/105* (2013.01); *G01N 2015/0053* (2013.01); *G01N 2015/0092* (2013.01)

(58) Field of Classification Search
    CPC .............. G01N 15/0211; G01N 33/18; G01N 2015/0053; G01N 2015/0092
    See application file for complete search history.

(56) References Cited

OTHER PUBLICATIONS

Long, Interactions between polystyrene microplastics and marine phytoplankton lead to species-specific hetero-aggregation, (Year: 2017).*

Ma et al. "Characteristics of microplastic removal via coagulation and ultrafiltration during drinking water treatment." Chemical Engineering Journal. Mar. 1, 2019;359:159-67.

Long et al. "Interactions between polystyrene microplastics and marine phytoplankton lead to species-specific hetero-aggregation." Environmental Pollution. Sep. 1, 2017;228:454-63.17.

* cited by examiner

METHOD OF EVALUATING AND OPTIONALLY SELECTING A SUITABLE CHEMISTRY FOR REMOVAL OF MICROPLASTICS IN A LIQUID MATRIX

RELATED APPLICATIONS

This application is a U.S. National Phase application of Int'l Appl. No. PCT/EP2020/054217, filed Feb. 18, 2020, which claims priority to Swedish Appl. No. 1950203-8, filed Feb. 18, 2019, and Swedish Appl. No. 1950532-0, filed May 6, 2019, each of which are incorporated herein by reference in their entireties.

FIELD OF THE INVENTION

The present invention relates to removal of microplastics from a liquid matrix.

BACKGROUND

There is a growing concern about microplastics in waters. Microplastics are defined as plastics of a particle size below 5 mm. The plastics may be different chemically, and physically, such as shape. The microplastics may also be classified based on origin, e.g. primary microplastics, and secondary microplastics. Primary microplastics are microplastics produced for an intended purpose, e.g. within cosmetics, where abrading beads for exfoliating purposes are added to shampoos, soaps, toothpastes, facial masks, etc. Secondary microplastics are microplastics formed by wear and physical degradation, e.g. of large plastic debris and synthetic textiles, such as degradation of car tyres and asphalt, and clothes when washing them. A single shower using microplastic containing cleaning compositions could result in 100 000 plastic particles entering the ocean. Thus, many countries are banning the use of microplastics for such purposes. However, a huge damage has already been done. The threat that poses to nature in terms of secondary microplastics.

Plastics are of concern due to their long lifetime, and low degree of chemical degradation in nature. Microplastics are found in waters, plants and wildlife today. Microplastics have been found present in remote locations including deep sea sediments and arctic sea ice. Thus, microplastics have entered the food chain. Microplastics, as other small sized particles, may be able to penetrate and/or be ingested, and accumulate in e.g. animals. Thus, predators on the top of the food chain, such as humans, are most sensitive to any effects of the microplastics. Their full effect on marine wildlife, humans, etc. is investigated but the full understanding thereof is still to be discovered.

The effluents of municipal wastewater treatment plants (WWTPs) are identified as one of the potential sources of microplastic contamination of flora and fauna.

Wastewater treatment plants generally involves two stages, called primary, and secondary treatment. Influent of a municipal WWTP may be black and grey waters.

A pre-treatment may be present which removes all materials that can be easily collected from the raw sewage or wastewater before they damage or clog any pumps and sewage lines of primary treatment apparatuses. Objects commonly removed during pretreatment include trash, tree limbs, leaves, branches, and other large objects. It includes screening to trap solid objects and may also include sedimentation by gravity to remove suspended solids.

The primary treatment is designed to remove gross, suspended and floating solids from raw sewage. This level is sometimes referred to as "mechanical treatment", although chemicals are often used to accelerate the sedimentation process. Primary treatment can reduce the biochemical oxygen demand (BOD) of the incoming wastewater by 20-30% and the total suspended solids (TSS) by some 50-60%. Primary treatment is usually the first stage of wastewater treatment. A separation step separates water and sludge. The sludge, primary sludge, obtained at the primary treatment, may be subjected to further treatment and reuse. The sludge may be composted, put on landfill, dewatered or dried to reduce the water content, and/or digested for methane production.

After the primary treatment, the wastewater is directed to a secondary treatment, which includes a biological treatment and removes the dissolved organic matter, phosphorus and nitrogen that escapes the primary treatment. This is achieved by microbes consuming the organic matter, and converting it to carbon dioxide, water, and energy for their own growth and reproduction. Secondary treatment may include a separation process ("secondary sedimentation") to remove the micro-organisms and more of the suspended solids from the treated water, as secondary sludge, prior to discharge or the tertiary treatment. More than 85% of the suspended solids and BOD can be removed by a well running plant with secondary treatment.

A tertiary treatment may sometimes be defined as anything more than primary and secondary treatment in order to allow release into a highly sensitive or fragile ecosystem (estuaries, low-flow rivers, coral reefs, etc.), or for reuse, e.g. as process water, or irrigation water. Treated water is sometimes disinfected chemically or physically (e.g. using UV, ozone, or chemically, e.g. by sodium hypochlorite or performic acid) prior to discharge into recipient or reuse. An example of a typical tertiary treatment process is the modification of a conventional secondary treatment plant to remove additional phosphorus and/or nitrogen.

It is reported by several research groups that removal rate of microplastics having a particle size larger than 10 µm is up to 85-99% in WWTP but due to the large water flow, the total amount of microplastic released via the effluent is very high. E.g. for a plant having an effluent flow of 260 000 m³/day with only 0.25 microplastic particles/l, the amount of microplastic in the effluent exiting the WWTP is 65 million microplastic particles/day. This is just from one wastewater plant. It is reported that existing treatment units in wastewater plants are not able to further remove the remaining microplastics. As shown, due to the large volumes of water treated, there still is a huge total amount of microplastics in the discharge.

Measurement of microplastics from WWTP effluent is very challenging as the concentration is low and the background noise (i.e. other compounds and particulates present in water) is high.

Today microplastics are normally measured by intensive pretreatment of water samples and visual inspection of sample with microscope. This method is limited to particles>20 µm. This method is laborious and time consuming and requires skilled persons to perform analysis.

Thus, there is an urgent need to limit the amounts of microplastics and improve removal of microplastics from e.g. waters of the world.

SUMMARY

The present invention relates to a way of evaluating and optionally selecting a suitable chemistry for removal of microplastics in a liquid matrix. The present invention is defined in the appended claims. By reducing the amount of microplastics in e.g. waters, the distribution to and accumulation in the flora and fauna may be limited. It has surprisingly been found that addition of coagulants and/or flocculants can remove microplastics e.g. this may be used as a last treatment step before releasing the treated water to the recipients or to reuse in a water treatment plant, to further remove microplastics from the effluent. It is important to find the most efficient way of removing microplastic particles from liquid matrices. A water treatment plant may have one or more treatment steps, e.g. primary, secondary and tertiary treatment steps, such as in industrial or municipal WWTPs. A water treatment plant may be a plant treating surface water, melted snow water, storm water, industrial process water, or raw water, or may be an industrial or municipal wastewater treatment plant. If the ingoing water of a water treatment plant is selected from e.g. surface water, storm water, raw water, drinking water, water originating from melted snow, effluent of industrial wastewater treatment plants, effluent of municipal wastewater treatment plants, industrial process water, or any combination thereof, the addition of coagulants and/or flocculants and a separation step connected thereto, can remove microplastics in said water(s) as a last treatment step of the water treatment plant before releasing the treated water to the recipients or to reuse the treated water for different purposes, or providing purified drinking water or process water. Said addition of coagulants and/or flocculants and the separation step may be provided after a primary treatment of the water as a last treatment step of a water treatment plant. Said addition of coagulants and/or flocculants and the separation step may be provided after a secondary treatment, following a primary treatment, of the water as a last treatment step of a water treatment plant. Said addition of coagulants and/or flocculants and the separation step may be provided after a tertiary treatment, following a primary and secondary treatment, of the water as a last treatment step of a water treatment plant. The present invention further uses a method of measuring the amount of microplastic particles present in waters using optical measurement to measure light scattering intensity and fluorescence intensity of a sample. In an embodiment the measurement may be flow cytometry method. The flow cytometry method allows measurement of the number and size of microplastics (also called count) in an aqueous phase in a short time and with a very low sample amount (milliliter). The method is based on measurement of number (count) and size of particles/drops/colloids in water. In addition, fluorescence intensity is measured. As the microplastics population in a cytogram may be located by their typical combined light scattering intensity and fluorescence the outcome of the measurement may be linked to microplastic count. The present invention may with the aid of an optical measuring method be able to select a suitable chemistry, i.e. different compounds alone or in different compositions, for removal of microplastics in a liquid matrix. Different liquid matrices may have different chemistries performing optimally. Thus, a selection of the optimal chemistry, i.e. compounds to add to the liquid matrix is of importance to improve a matrix treatment process, such as a purification process. A water treatment plant treating at least one of surface water, storm water, raw water, water for drinking water, water originating from melted snow, effluent of industrial wastewater treatment plants, effluent of municipal wastewater treatment plants, industrial process water, or any combination thereof, may be monitored according to the present method, and optionally the addition of the coagulants and/or flocculants may be controlled, but the outgoing water may also be evaluated with the present method.

The present invention also relates to use of a chemistry comprising a chemical system comprising at least one coagulant and/or flocculant for removal of microplastics.

SHORT DESCRIPTION OF THE DRAWINGS

DETAILED DESCRIPTION

Figure 1:
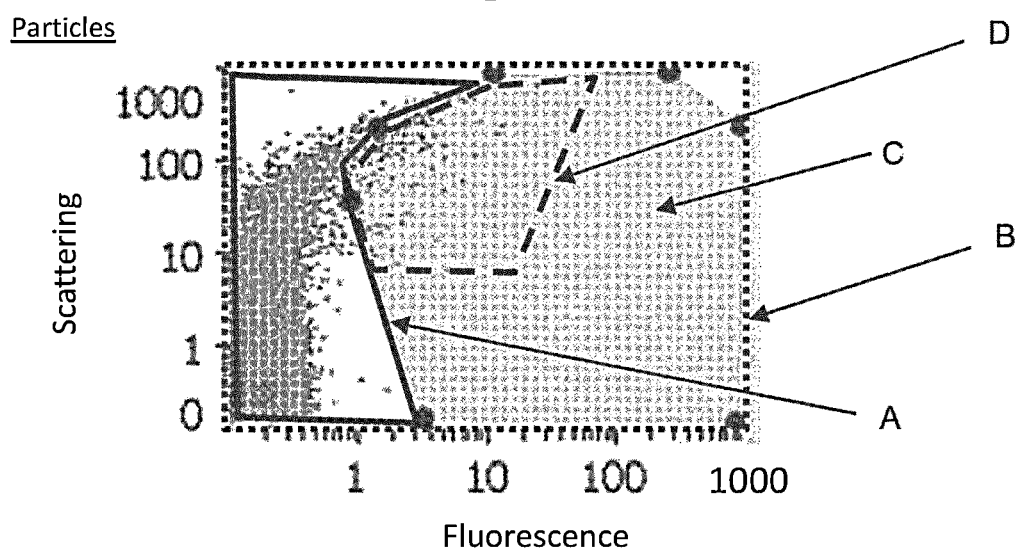
FIG. 1 shows a flow cytogram of secondary wastewater effluent without added microplastic particles.

The present invention relates to a method of evaluating and optionally selecting a suitable chemistry for removal of microplastics in a liquid matrix. The present method comprises the steps of:
a. providing a predetermined volume of a liquid matrix,
b. adding a preset amount of a chemical system comprising at least one coagulant and/or flocculant to the liquid matrix of step a), and allowing the added chemical system to interact to form flocs and/or aggregates containing any microplastic particles, if present in the liquid matrix,
c. removing flocs and/or aggregates containing any microplastic particles of the liquid matrix in a separation step to form a clarified liquid matrix,
d. measuring fluorescence intensity and light scattering intensity of any particles in a sample volume of clarified liquid matrix by an optical measurement,
e. assessing the efficiency of microplastics removal based on:
the number of microplastic particles in the sample volume used in step d),
or
the number of microplastic particles in the sample volume used in step d) compared to a known number of microplastic particles, if used, added to the liquid matrix in step a).

The number of microplastic particles referred to herein may also be called count, which is common for optical measurement, such as flow cytometry.

The method may further comprise the step of:
a'. introducing to the predetermined amount a known number of microplastic particles, performed after step a and before step b.

The method may further comprise at least one step performed after step d) and before step e) of:
d'. gathering and combining the scattering intensity data and the fluorescence intensity data of the particles,
d''. identifying particle populations of the measured data representing microplastic particles populations based on predetermined identification data,
d'''. determining the number of microplastic particles of the microplastic particles populations, preferably said method comprising all steps d', d'' and d''' in said order.

The method may further comprise the step of:
e'. performing the same separation step as in c), and performing a measurement in accordance with step d), or d) to d'), or d) to d"), or d to d'"). The step e') may preferably be performed after step e) but before any subsequent steps, such as steps f) and g) mentioned below.

The liquid matrix may be mixed during at least one of step a'), and b).

Steps a) to e), or if present e'), may be repeated a number of times with other chemical systems than said at least one chemical system, and further comprising the steps of:
f. comparing the efficiency of microplastics removal of all chemical systems tested, and
g. selecting a suitable chemical system for the desired removal efficiency in a liquid matrix.

The predefined identification data comprises at least one of:
comparing with reference data of scattering intensity and the fluorescence intensity of said known microplastic particles, and identifying an area of a plotted graph of the scattering intensity and the fluorescence intensity representing the microplastic particles populations; or
comparing the scattering intensity and the fluorescence intensity data of microplastic particles of the liquid matrix in step a) and optionally step a') measured by taking a sample of the liquid matrix in step a) and optionally a sample of the liquid matrix in step a') and performing measurements in accordance with steps d) and optionally d'); or
comparing the scattering intensity and the fluorescence intensity data of microplastic particles of a liquid matrix other than the liquid matrix of step a), and another sample of said other liquid matrix, being than the liquid matrix of step a) and introducing thereto a predetermined amount a known number of microplastics, by taking samples of the liquid matrices, doped and undoped with microplastic particles, and performing measurements in accordance with steps d) and optionally d'). The other matrices used for the predefined identification data may be water or synthetic water. The amounts and types of microplastic particle used in the predefined identification data may be the same or different to the microplastic particles mentioned for the present process step a').

The present method comprises the steps of:
i. providing a predetermined volume of a liquid matrix,
ii. introducing to the predetermined amount a known number of microplastic particles,
iii. adding a preset amount of a chemical system comprising at least one coagulant and/or flocculant to the liquid matrix of step ii),
iv. allowing the added chemical system of step iii) to interact with the microplastic containing liquid matrix to form flocs and/or aggregates containing microplastic particles,
v. removing flocs and/or aggregates containing microplastic particles of the liquid matrix in a separation step to form a clarified liquid matrix,
vi. taking a sample volume of the clarified liquid matrix,
vii. measuring fluorescence intensity and light scattering intensity of particles in the sample volume by an optical measurement,
viii. gathering and combining the scattering intensity data and the fluorescence intensity data of the particles,
ix. identifying particle populations of the measured data representing microplastic particles populations based on predetermined identification data,
x. determining the number (i.e. count) of microplastic particles of the microplastic particles populations, and
xi. assessing the efficiency of microplastics removal based on:
the number (i.e. count) of microplastic particles in the sample used in step vi),
or
the number (i.e. count) of microplastic particles in the sample used in step vi) compared to the number (i.e. count) of microplastic particles of the liquid matrix in step ii) measured by taking a sample of the liquid matrix in ii), performing the same separation step as in v), and
performing a measurement in accordance with steps vii) to x), i.e. without addition of a chemical system.

The number of microplastic particles referred to herein may also be called count, which is common for optical measurement, such as flow cytometry.

The predefined identification data comprises at least one of:
comparing with reference data of scattering intensity and the fluorescence intensity of said known microplastic particles, and identifying an area of a plotted graph of the scattering intensity and the fluorescence intensity representing the microplastic particles populations; or
comparing the scattering intensity and the fluorescence intensity data of microplastic particles of the liquid matrix in step i) and step ii) measured by taking a sample of the liquid matrix in step i) and a sample of the liquid matrix in step ii) and performing measurements in accordance with steps vii) and viii); or
comparing the scattering intensity and the fluorescence intensity data of microplastic particles of a liquid matrix other than the liquid matrix of step i), and another sample of said other liquid matrix, being than the liquid matrix of step i) and introducing thereto a predetermined amount a known number of microplastics, by taking samples of the liquid matrices, doped and undoped with microplastic particles, and performing measurements in accordance with steps vii) and viii). The other matrices used for the predefined identification data may be water or synthetic water. The amounts and types of microplastic particle used in the predefined identification data may be the same or different to the microplastic particles mentioned for the present process step ii).

The liquid matrix may be mixed during at least one of step ii), step iii) and iv).

Steps i) to xi) may be repeated a number of times with other chemical systems than said at least one chemical system, and further comprising the steps of:
xii. comparing the efficiency of microplastics removal of all chemical systems tested, and
xiii. selecting a suitable chemical system for the desired removal efficiency in a liquid matrix.

The liquid matrix may be a water matrix, such as a raw water, drinking water, storm water, water originating from melted snow, surface water, effluent of industrial wastewater treatment plants, effluent of municipal wastewater treatment plants, industrial process water. The water matrix may be industrial and/or municipal waters, such as effluents of wastewater treatment plants after secondary treatment, or tertiary treatments; preferably secondary treatments. The water matrix to be treated according to the present method is preferably effluent from water treatment plants, i.e. the present process would be used after the conventional last treatment step of the water treatment plants before releasing the treated water to the recipients or to reuse in a water treatment plant.

The removal of flocs and/or aggregates of step c or v) may be performed by a separation method selected from sedimentation, filtration, flotation, froth flotation, dissolved air flotation, or any combination thereof; preferably sedimentation. A clarifier may be used.

The selected chemistry system is preferably used for treating an industrial scale liquid matrix for microplastics removal. The selected chemistry system is preferably used for treating a full scale liquid matrix for microplastics removal.

The coagulant may be selected from inorganic coagulants.

The inorganic coagulant may comprise iron containing salts, aluminium containing salts, magnesium containing salts, or any derivative thereof, preferably chlorides, sulphates, chlorosulphates, chlorohydrates, silicates, nitrates, and any derivate thereof. The inorganic coagulant may comprise aluminium sulfate, polyaluminium sulfate, aluminium chloride, polyaluminium chloride, polyaluminium chlorosulfate, polyaluminium hydroxychlorosulfate, aluminium chlorohydrate, sodium aluminate, ferric sulfate, polyferric sulfate, ferric chloride, ferric chlorosulphate, polyferric chloride, ferrous sulfate, ferrous chlorosulphate, ferrous chloride, aluminium triformate, polyaluminium formate, polyaluminium nitrate, polyaluminium silicate, magnesium chloride, any derivative thereof, and any combination thereof. The inorganic coagulant may comprise iron containing salts, aluminium containing salts, or any derivative thereof, preferably chlorides, sulphates, chlorosulphates, chlorohydrates, and any derivate thereof; more preferably aluminium sulfate, polyaluminium sulfate, aluminium chloride, polyaluminium chloride, polyaluminium chlorosulfate, polyaluminium hydroxychlorosulfate, aluminium chlorohydrate, ferric sulfate, polyferric sulfate, ferric chloride, ferric chlorosulphate, polyferric chloride, ferrous sulfate, ferrous chlorosulphate, ferrous chloride, any derivative thereof, and any combination thereof.

The flocculant may be a polymer, such as a polymer which may comprise anionic polymers, amphoteric polymer, cationic polymers, nonionic polymers, polysaccharides, polyphenolic compounds, and any combination thereof.

The polymer may comprise anionic polymer which may comprise polymers based on compounds selected from the group acrylamide (AMD), (2-acrylamido-2-methyl-1-propanesulfonic acid) (AMPS) and acrylic acid (AA) and any combination thereof; such as polymers based on the combination of acrylamide (AMD) and (2-acrylamido-2-methyl-1-propanesulfonic acid) (AMPS) and/or combination of acrylic acid (AA) and (2-acrylamido-2-methyl-1-propanesulfonic acid) (AMPS).

The polymer may comprise cationic polymer which may comprise cationic polyacrylamide, poly(diallyldimethylammonium chloride), polyamine, melamine-formaldehyde resin, polydicyandiamide, and any combination thereof.

The polymer may comprise nonionic polymer comprising polymers based on compounds comprising acrylamide (AMD).

The polysaccharides may be selected from the group cellulose, starch, chitin and chitosan compounds and any combination thereof. The polyphenolics may be selected from the group tannins, lignin, and any combination thereof.

The polymer may comprise polyacrylamide, polyamine, polyDADMAC, any derivative thereof, or any combination thereof.

Said at least one coagulant and/or flocculant may be selected from the group:

aluminium sulfate, polyaluminium sulfate, aluminium chloride, polyaluminium chloride, polyaluminium chlorosulfate, polyaluminium hydroxychlorosulfate, aluminium chlorohydrate, ferric sulfate, polyferric sulfate, ferric chloride, ferric chlorosulphate, polyferric chloride, ferrous sulfate, ferrous chlorosulphate, ferrous chloride;

anionic polymer comprising polymers based on compounds selected from the group acrylamide (AMD), (2-acrylamido-2-methyl-1-propanesulfonic acid) (AMPS) and acrylic acid (AA);

cationic polymer comprising polyacrylamide, poly(diallyldimethylammonium chloride), polyamine, melamine-formaldehyde resin, polydicyandiamide;

nonionic polymer comprising polymers based on compounds comprising acrylamide (AMD);

cellulose, starch, chitin and chitosan compounds;

tannins, and lignin; and any combination thereof. Preferably, said at least one coagulant and/or flocculant may be selected from the group polyaluminium sulfate, polyaluminium chloride, ferric sulfate, polyferric sulfate, ferric chloride, polyferric chloride, cationic polymer comprising polyamine, and any combination thereof.

The coagulant may be admixed in the amount to provide for a concentration of metal of the coagulant in the microplastic containing water of 0.01-1.5 mmol/l, preferably 0.01-1.2 mmol/l, preferably 0.05-1 mmol/l, preferably 0.1-0.9 mmol/l, preferably 0.1-0.8 mmol/l, preferably 0.2-0.6 mmol/l, preferably 0.3-0.5 mmol/l.

Coagulants are preferably used at pH between about 4.5 to 7.5.

Iron and aluminium coagulants may provide improved efficiency of MP removal or small amount of the coagulant needed, when used at pH<7, e.g. pH 4.5. to less than 7, pH 5 to less than 7, preferably pH 5 to 6.9, or pH 5.0 to 6.5, or pH 5.5 to 6.2, compared to when used at pH 7 or more, e.g. compared to pH 7.0 to 7.3.

Basicity of polyaluminiumchloride may have influence on MP removal. In some embodiments, one or more poly aluminium coagulants (PAC) may comprise 25%-45% basicity (i.e., OH/Al ratio of about 0.75 to about 1.35). In some embodiments, PAC coagulants may comprise up to about 70% basicity (i.e., an OH/Al ratio of about 2.10).

In some embodiments, one or more PACl-based coagulants for use in the methods described herein may comprise from about 0.1% or less to about 85% or more basicity (e.g., an OH/Al ratio of about 2.55) or more. In some embodiments, one or more PACl-based coagulants for use in the methods described herein may comprise 0% basicity.

The amount of active polymer, i.e. amount of polymer in terms of actives or active material (excluding non-active parts like water of a polymer containing product) meaning amount of polymer in dry form, i.e. calculated as dry solids, added to the waters may be about 0.00001-40 wt %, preferably, 0.00005-40 wt %, preferably 0.00005-20 wt %, most preferably 0.00005-0.6 wt %. The amount of active polymer added to the waters may be about 0-50 mg/l, preferably 0.1-50 mg/l, preferably 1-50 mg/l, preferably 5-50 mg/l, preferably 10-45 mg/l, most preferably 10-25 mg/l.

The present method may further comprise addition of an additive comprising iron containing salts, aluminium containing salts, or magnesium containing salts comprising hydroxides and/or oxides, preferably ferric hydroxide, ferrous hydroxide, magnesium oxide, magnesium hydroxide.

The microplastics present in the waters may comprise polyethylene, polypropylene, polyvinylchloride, polyurethane, polyester, polyamide, polyester, acrylonitrile butadiene styrene, polytetrafluoroethylene, cellulose acetate, polycarbonate, polymethylmethacrylate, polyethylene terephthalate, polyvinylidene chloride, phenol formaldehyde, melamine formaldehyde and any derivative thereof.

The size of the microplastic particles may be 0.1-100 μm, such as 0.1-50 μm, 1-50 μm, 5-100 μm, 5-50 μm, 6-100 μm, 5-20 μm, 6-50 μm, or 6-30 μm.

The microplastic content or number after the present treatment may be decreased to an amount below present detection limits. This would give an appearance that there are no microplastics present after the present treatment.

The present optical measurement may include a selection of type of light scattering and fluorescence channel.

The present optical measurement measuring light scattering and fluorescence of particles may measure forward and/or side scattering. The scattering may then be used to determine an area of plotting symbolizing the microplastic particles.

The present optical measurement measuring light scattering and fluorescence of particles may further provide a determination of the microplastic particles' sizes, and/or amount of particles of the same size (also referred to a density of a plotted area).

If the measurement of number of microplastic particles in the water is done in more than one position multiple optical measurement devices may be used, or one optical measurement device may be used for analysis of all measurement positions.

The optical measurement may be a flow cytometry measurement. The count of microplastic particles in a predetermined volume sample may be performed using the flow cytometry method.

The flow cytometry method may include particle identification, particle classification, particle size determination, particle size distribution, particle count quantification, or any combination thereof.

The predetermined sample volume of the optical measurement may be about 1 ml, of which 200 μl may be used for the analysis.

The microplastic containing water or treated water, prior to the optical measurement, e.g. measuring the count of microplastic particles, may be provided with a fluorescent dye for selective staining of the microplastics. The microplastics have a hydrophobic surface. A dye may be used for easier detection of the microplastic particles. Preferably a dye to be used is attracted to hydrophobic surfaces. The fluorescent dye may be a lipophilic stain, such as Nile Red, Rose Bengal, Oil red EGN, Eosin B, Hostasol Yellow 3G, a BODIPY green dye, any derivative, or combination thereof.

In the use according to the present invention the removal of microplastics is from a liquid matrix, preferably water matrix, water matrix preferably comprises one or more of microplastic containing raw water, drinking water, storm water, water originating from melted snow, surface water, effluent of industrial wastewater treatment plants, effluent of municipal wastewater treatment plants, industrial process water.

In said use at least one coagulant and/or flocculant is selected from: flocculant being a polymer, preferably selected from the group anionic polymers, cationic polymers, nonionic polymers, amphoteric polymers, polysaccharides, polyphenolic compounds, and any combination thereof; anionic polymer preferably comprises polymers based on compounds selected from the group acrylamide (AMD), (2-acrylamido-2-methyl-1-propanesulfonic acid) (AMPS) and acrylic acid (AA) and any combination thereof; cationic polymer preferably comprises cationic polyacrylamide, poly(diallyldimethylammonium chloride), polyamine, melamine-formaldehyde resin, polydicyandiamide, and any combination thereof; nonionic polymer comprises polymers based on compounds comprising acrylamide (AMD); polysaccharides preferably comprises cellulose, starch, chitin and chitosan compounds, and any combination thereof; and polyphenolics preferably comprises tannins, lignin, and any combination thereof, coagulant being selected from inorganic coagulants; preferably inorganic coagulants comprising iron containing salts, aluminium containing salts, magnesium containing salts, or any derivative thereof, preferably chlorides, sulphates, chlorosulphates, chlorohydrates, silicates, nitrates, and any derivate thereof; more preferably aluminium sulfate, polyaluminium sulfate, aluminium chloride, polyaluminium chloride, polyaluminium chlorosulfate, polyaluminium hydroxychlorosulfate, aluminium chlorohydrate, sodium aluminate, ferric sulfate, polyferric sulfate, ferric chloride, ferric chlorosulphate, polyferric chloride, ferrous sulfate, ferrous chlorosulphate, ferrous chloride, aluminium triformate, polyaluminium formate, polyaluminium nitrate, polyaluminium silicate, magnesium chloride, any derivative thereof, and any combination thereof; and any combination thereof.

In said use the coagulant is admixed in the amount to provide for a concentration of metal of the coagulant in the microplastic containing water of 0.01-1.5 mmol/l, such as 0.01-1.2 mmol/l, 0.05-1 mmol/l, 0.1-0.9 mmol/l, 0.1-0.8 mmol/l, 0.2-0.6 mmol/l, or 0.3-0.5 mmol/l.

In said use the amount of active polymer added to the waters may be about 0-50 mg/l, such as 0.1-50 mg/l, 1-50 mg/l, 5-50 mg/l, 10-45 mg/l, or 10-25 mg/l.

In said use the chemical system is using a last separation step before releasing the treated liquid matrix to the recipients, or to reuse.

EXAMPLES

Materials

The following coagulants and flocculants were used in the coagulation and flocculation experiments:

Ferric chloride (13.8% Fe, density 1.42 kg/dm3)
Ferric sulphate (11.4% Fe, density 1.50 kg/dm3)
Polyaluminium chloride (9.3% Al, density 1.39 kg/dm3)
Polymer (polyamine Kemira SuperFloc C-577) (total solids content 49-52%)

The chemical dosages are presented as dosed metal amount in millimoles per liter, mmol Me/L, where Me corresponds to Fe-dosage when ferric chloride or ferric sulphate was used and Al-dosage when polyaluminium chloride was used.

The polymer was used as 1.0% solution.

The following microplastic particles were used in the experiments, unless otherwise stated:

MP1: 1 μm polystyrene, red fluorescent, 1% TS ThermoFisher, Catalogue number R0100

MP3: 6 μm (6.28 μm reported in bottle) polystyrene, yellow, 2.6% TS, PolyScience, Catalogue number 15716-5

MP4: 10 μm (9.9 mm reported in bottle) polystyrene, violet, 2.7% TS, PolyScience, Catalogue number, 18139-2

MP5: 15 μm (15.4 μm reported in bottle) polystyrene, 2.6% TS, PolyScience, Catalogue number, 18328-5

1 M NaOH and 1 M HCl were used for pH adjustment.

The experiments were monitored using flow cytometry (Sysmex-Partec CyFlow SL). Different kinds of results were calculated from the flow cytograms:
- all the measured counts in the flow cytogram, are called "Counts (all)" including all counts created by all the particles in the sample
- counts that appear in a selected area of the flow cytogram, in an area called MP gate, are called "Counts (MP gate)". MP gate is an area in the flow cytogram that is sensitive to microplastic particles and their amounts in the sample.
- counts that are created due to the chemical treatment that creates other particles than microplastic particles at MP gate, are called "Disturbing counts (MP gate)". These counts are measured when carrying out the actual chemical treatment without having any added microplastic particles in the solution. These counts show the disturbance from the treatment itself on the result.
- counts of particles having a certain particle size, can be detected. In the examples, counts in the MP gate having a particle size above 3.0 µm have been calculated and are called "Counts>3.0 µm (MP gate)", and similarly, "Counts<1.0 µm (all)" represent the counts of particles with a size of less than 1.0 µm in the whole flow cytogram, and "Counts<0.45 µm (all)" represent the counts of particles with size of less than 0.45 µm in the whole flow cytogram.

The unit in presented counts is counts/mL.

The unit MP/L means microplastic particles in a litre.

From the results, microplastics removal efficiency was calculated as follows:

$$(Counts(MP\ gate)_{Zero} - Counts(MP\ gate)_{Treatment}) / (Counts(MP\ gate)_{Zero}) \times 100\%,$$

where Zero is a sample treated similarly than other samples but without chemical.

Example 1. Measurement of Water Samples Using Flow Cytometry a) Secondary Effluent from a Wastewater Treatment Plant A flow cytogram of the secondary effluent from a wastewater treatment plant is presented in FIG. 1. The grey area in the flow cytogram is an example of a selected measurement area for microplastic particles, called MP gate. From FIG. 1 it is seen that only very few particles from the sample appear in the grey area and the majority of the particles are on the left-hand side of it. The particles outside the grey area are not counted in the results of the grey area. From FIG. 1, it is clear that the measured solution does not contain any (almost at all) particles that would appear in the selected region of the MP gate.

FIG. 1 shows a flow cytogram of secondary wastewater effluent without added microplastic particles. The black solid line shows the area where most of the particles from the effluent give a signal in the flow cytogram, see to the left of the graph—A. The rectangular area with small square dashed line shows the area of the whole flow cytogram. All the measured particles are measured in this area, see the outer sides of the graph—B. MP gate, shown as the grey area, i.e. the area enclosed by the larger dots of the graph—C. Microplastic particles are measured in a selected MP gate. The dashed line shows an area, where some disturbing signals from the secondary wastewater effluent are measured in the MP gate, see the upper left corner of the MP gate—D.

Figure 2:
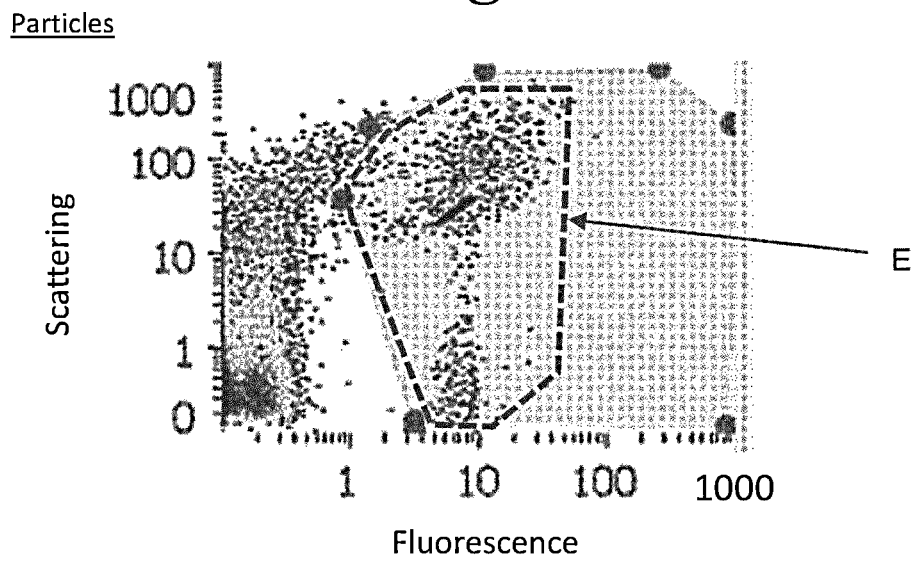
FIG. 2 shows an example of a flow cytogram showing an area where most of the MP3 microplastic particles give a signal.

FIG. 2 shows a measurement of a secondary effluent from a wastewater treatment plant with added microplastic particles MP3. It is seen that MP3 appears in a different area, in the MP gate, of a flow cytogram than the particles from the effluent, and the particle counts created by MP3 can be measured.

FIG. 2 shows an example of a flow cytogram showing an area where most of the MP3 microplastic particles give a signal, see area within dashed line—E.

For the flow cytogram measurements, a sample of 0.5 ml was taken, into which 0.5 ml of ultrapure water (Millipore, Milli-Q, Q-POD) was added into flow cytometry test tubes, and thereafter the sample was measured using flow cytometry. The sample of MP3 containing secondary wastewater effluent was taken while stirring.

Figure 3:
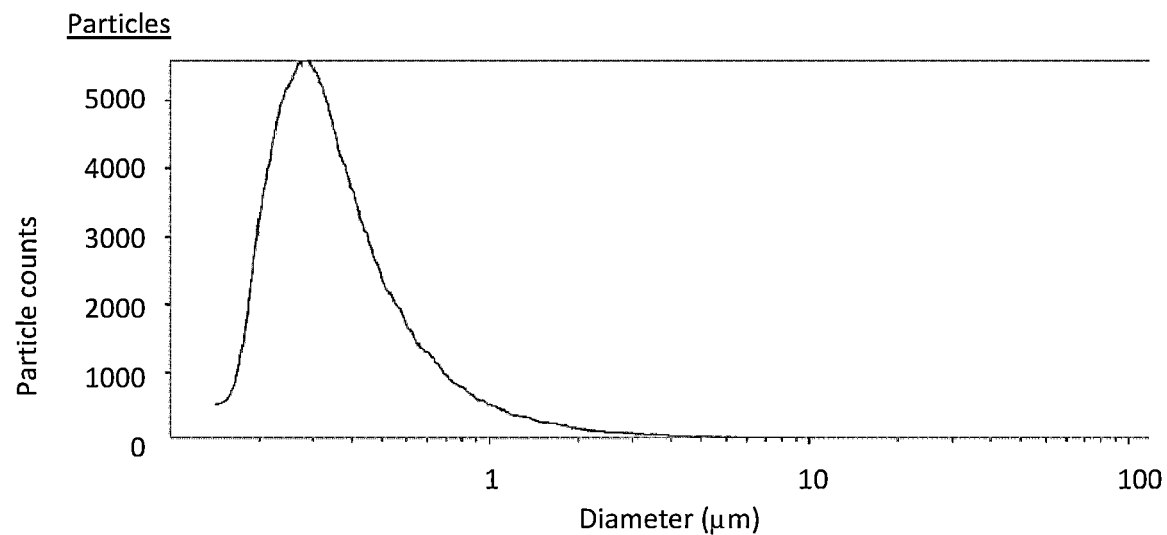
FIG. 3 shows the measured particle size of secondary wastewater effluent when using Counts (all).

FIG. 3 shows the measured particle size distribution of the secondary wastewater effluent in the flow cytogram when calculating Counts (all). No microplastic particles were added into this sample. It can be seen that the majority of the particles are less than 1 µm in size.

The measured counts are presented in Table 1. The secondary wastewater effluent did not contain any added microplastic particles, and therefore the Counts (MP gate) are very low, only 0.06% of the Counts (all). the counts>3.0 µm (MP gate) are even less, only 0.05% of the Counts (all).

This means that the secondary wastewater effluent itself gives very minor disturbance and influence in the counts at the selected MP gate.

TABLE 1

The measured results of secondary wastewater effluent in the whole flow cytogram and in the MP gate.

| Water | Counts (all) | Counts <1.0 µm (all) | Counts <0.45 µm (all) | Counts (MP gate) | Counts >3.0 µm (MP gate) |
|---|---|---|---|---|---|
| Secondary wastewater effluent | 1553200 | 1500560 | 1315180 | 860 | 800 |

Figure 4:
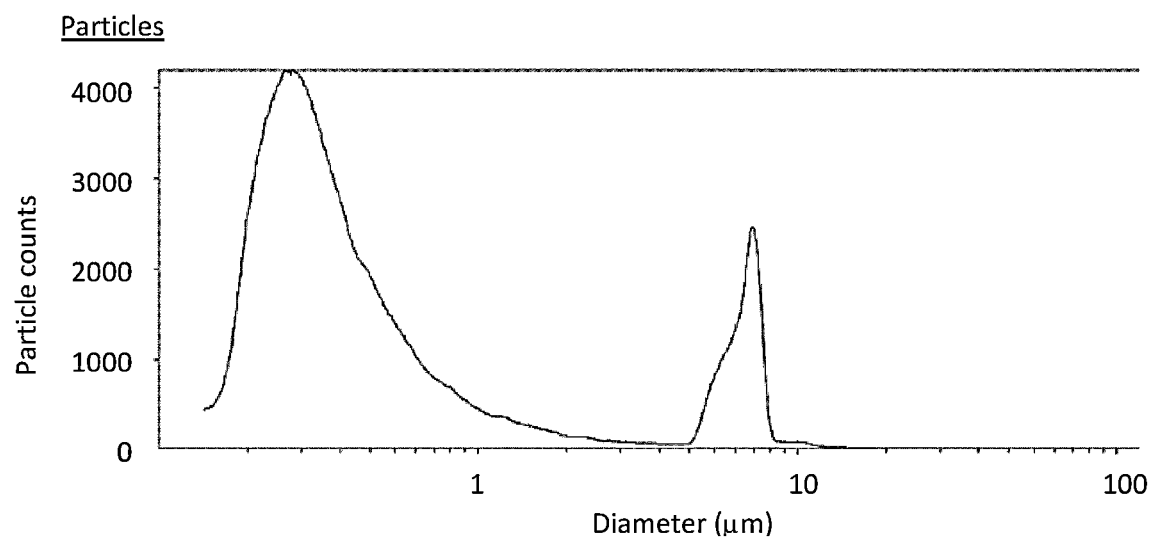
FIG. 4 shows the measured particle size of secondary wastewater effluent when using Counts (all) and with added MP3.

Furthermore, as presented in Table 1, when looking at the share of counts originating from particles having a particle size lower than 1.0 µm (Counts<1.0 µm (all)) in secondary wastewater effluent, these particles represent 97% of all counts of the flow cytogram (Counts (all)). Similarly, the share of counts originating from particles having lower particle size than 0.45 µm (Counts<0.45 µm (all)), still represent 85% of all counts of the flow cytogram (Counts (all)). Therefore, in the whole flow cytogram, the larger particles than what is present in the effluent, can be measured and distinguished from the secondary wastewater effluent, even without using the MP gate. This is illustrated in FIG. 4 with a secondary wastewater effluent that contained MP3.

b) Other Water Samples

Other water samples were also measured using flow cytometry: lake water and samples called Matrix 1a and Matrix 2a.

Preparation of Matrix 1a: 500 mL of ultrapure water (Millipore, Milli-Q, Q-POD) was taken using a measuring glass and poured into a 10 L bucket. Then, 0.13 g of CH3COONa and 0.22 g of NaHCO$_3$ were dissolved into 500 mL of ultrapure water in a beaker and poured into the bucket. Finally, 9000 mL of ultrapure water was added using 500 mL and 2000 mL measuring glasses. For flow cytometry analysis, a sample of 1 ml was taken and measured using flow cytometry.

Preparation of Matrix 2a: 500 mL of ultrapure water (Millipore, Milli-Q, Q-POD) was taken using a measuring glass and poured into a 10 L bucket. Then, 0.13 g of $CH_3COONa$ and 0.22 g of $NaHCO_3$ were dissolved into 500 mL of ultrapure water in a beaker and poured into the bucket. Then, 0.3314 g of HA was weighed into a beaker, 1.6 mL of 1 mol/L NaOH and approximately 300 mL of ultrapure water were added. The solution was mixed using a magnetic stirrer. After mixing well, this HA solution was poured into a volumetric flask and diluted to 1000 mL and added to the bucket. Finally, 8000 mL of ultrapure water was added to the bucket using 2000 ml measuring glasses. For flow cytometry analysis, a sample of 0.5 ml was taken, into which 0.5 ml of ultrapure water (Millipore, Milli-Q, Q-POD) was added into flow cytometry test tubes, and thereafter the sample was measured using flow cytometry.

In the case of lake water, a sample of 1 ml was taken and measured using flow cytometry.

The results are presented in the Table 2.

TABLE 2

The measured results of other water samples.

| Water | Counts <1.0 μm (all) | Counts <0.45 μm (all) | Counts (all) | Counts (MP gate) | Counts >3.0 μm (MP gate) |
| --- | --- | --- | --- | --- | --- |
| Matrix 1a | 48220 | 47900 | 46385 | 0 | 0 |
| Matrix 2a | 1368360 | 1056990 | 519550 | 1400 | 1080 |
| Lake water | 585860 | 476970 | 268260 | 1210 | 630 |

Similarly, as was the case with secondary wastewater effluent, other water samples caused only very low counts at the selected MP gates.

Example 2. Measurement of MP1, MP3, MP4 and MP5 in Secondary Wastewater Effluent Using Flow Cytometry Several different solutions containing microplastic particles were prepared and measured using a flow cytometry.

a) Measurement of MP1 Particles

MP1 was poured into a small beaker. From this beaker, 495 μL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, 20 mL of this solution was pipetted into another sealable bottle containing 980 mL of ultrapure water, measured by (with) measuring glass, and the pipette tip was flushed a few times.

The first sample (Table 3), was prepared pipetting 5289 μL of this solution to the 100-mL volumetric flask, 28 μL of 1 mol/L HCl was added, and the bottle was filled to the mark with effluent water. Other samples were prepared pipetting, depending on the desired microplastic amount in the sample, 26-3967 μL of the solution to a sealable bottle, and 28 μL of 1 mol/L HCl was added. Then, depending on the desired microplastic amount in the sample, 1033-4974 μL of ultrapure water was pipetted to the bottle. Finally, 95 mL of effluent was added. The details of sample preparation for each sample are shown in Table 3.

A sample of 0.5 ml was taken, into which 0.5 ml of ultrapure water (Millipore, Milli-Q, Q-POD) was added into flow cytometry test tubes, and thereafter the sample was measured using flow cytometry. The measurement results are shown in Table 3.

TABLE 3

Volume of MP1 containing solution, ultrapure water and secondary wastewater effluent used in the sample preparation, and the measured counts at the selected MP gate.

| Volume MP1 containing solution, mL | Volume ultrapure water, mL | Volume effluent, mL | Comments | Counts (MP gate) |
| --- | --- | --- | --- | --- |
| 5.289 | 0.000 | 94.71 | Use volumetric flask, and fill to the mark with effluent | 126897 |
| 3.967 | 1.033 | 95 | Measuring glass for effluent | 90215 |
| 2.644 | 2.356 | 95 | Measuring glass for effluent | 91075 |
| 1.322 | 3.678 | 95 | Measuring glass for effluent | 31973 |
| 0.793 | 4.207 | 95 | Measuring glass for effluent | 19907 |
| 0.397 | 4.603 | 95 | Measuring glass for effluent | 10397 |
| 0.212 | 4.788 | 95 | Measuring glass for effluent | 5577 |
| 0.106 | 4.894 | 95 | Measuring glass for effluent | 2690 |
| 0.026 | 4.974 | 95 | Measuring glass for effluent | 713 | b) Measurement of MP3 Particles

MP3 was poured into a small beaker. From this beaker, 47 μL of the product was pipetted into a small beaker containing effluent wastewater, and the pipette tip was flushed a few times. Then, this solution was poured into a 50-mL volumetric flask that was filled to the mark with secondary wastewater treatment plant effluent. This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, a sample of 0.5 ml was taken, into which 0.5 ml of ultrapure water (Millipore, Milli-Q, Q-POD) was added into flow cytometry test tubes, and thereafter the sample was measured using flow cytometry.

So prepared sample was also diluted to lower concentrations using secondary wastewater effluent. These samples were measured similarly as the original sample described above. The response from Counts (MP gate) for MP3 is linear as a function of MP3 concentration in the samples. All the results are presented in Table 4.

c) Measurement of MP4 Particles

MP4 was poured into a small beaker. From this beaker, 178 μL of the product was pipetted into a small beaker containing effluent wastewater, and the pipette tip was flushed a few times. Then, this solution was poured into a 50-mL volumetric flask that was filled to the mark with secondary wastewater effluent. This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, a sample of 0.5 ml was taken, into which 0.5 ml of ultrapure water (Millipore, Milli-Q, Q-POD) was added into flow cytometry test tubes, and thereafter the sample was measured using flow cytometry. The results are presented in Table 4.

d) Measurement of MP5 Particles

MP5 was poured into a small beaker. From this beaker, 695 μL of the product was pipetted into a small beaker containing effluent wastewater, and the pipette tip was flushed a few times. Then, this solution was poured into a 50-mL volumetric flask that was filled to the mark with secondary wastewater treatment plant effluent. This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, a sample of 0.5 ml was taken, into which 0.5 ml of ultrapure water (Millipore, Milli-Q, Q-POD) was added into flow cytometry test tubes, and thereafter the sample was measured using flow cytometry. The results are presented in Table 4.

TABLE 4

Counts of different microplastic particles in secondary wastewater effluent at the selected MP gate.

| Microplastic particles used | Calculated concentration of microplastic particles, MP/L | Counts (MP gate) | Counts >3.0 μm (MP gate) |
|---|---|---|---|
| MP3 | 479 100 | 1290 | 1140 |
| MP3 | 958 200 | 1660 | 1470 |
| MP3 | 9 582 000 | 7060 | 6850 |
| MP3 | 18 110 000 | 12200 | 11850 |
| MP3 | 47 910 000 | 29530 | 29050 |
| MP3 | 181 100 000 | 124670 | 123070 |
| MP4 | — | 26260 | 25160 |
| MP5 | — | 128170 | 126640 |

The microplastic particle concentrations (MP/L) were calculated based on the particle diameter, particle material density (polystyrene density 1.04 g/cm$^3$), the solids content of the microplastics products, and known dilution of the microplastics products.

The presented results show that it is possible to measure microplastic particles using a flow cytometry.

Example 3. Removal of Microplastic from Water Matrices by Coagulation and Flocculation Using Polyaluminium Chloride, Ferric Chloride, Ferric Sulphate and Polyamine The experiments were carried out using 1 L beakers that were combined with Kemira flocculator that was used as a mixing device. Mixing parameters are shown in Table 5. In the experiments, first the fast mixing was turned on. Without any break, the fast mixing was followed by the slow mixing. Again, without any break, the settling period followed the slow mixing. The experiment ended in the end of the settling. The selected amounts of coagulant or flocculant, and pH adjustment chemical was dosed to the samples simultaneously in the beginning of the fast mixing. After the settling, approximately 0.1 L-samples were taken for analysis using a glass pipette, 3 cm below the surface for analysis. The tip of the used glass pipette was cut to allow for also big flocs enter the pipette. Pipette was then emptied to a glass bottle by releasing the pipette filler.

In the case of Matrix 1 and Lake water (Matrix 4), for flow cytometry analysis, a sample of 1 ml was taken and measured using flow cytometry.

In the case of Matrix 2 and Secondary wastewater effluent (Matrix 3a-Matrix 3d), for flow cytometry analysis, a sample of 0.5 ml was taken, into which 0.5 ml of ultrapure water (Millipore, Milli-Q, Q-POD) was added into flow cytometry test tubes, and thereafter the sample was measured using flow cytometry.

When other than MP1 microplastic particle was used, the sample was taken while stirring.

TABLE 5

Mixing parameters used in experiments.
rpm = rounds (revolutions) per minute.

| Parameter | Speed, rpm | Time, min |
|---|---|---|
| Fast mixing | 400 | 0.5 |
| Slow mixing | 40 | 20 |
| Settling | 0 | 30 | a) Matrix 1

Preparation of Matrix 1: MP1 was poured into a small beaker. From this beaker, 495 μL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, 20 mL of this solution was pipetted into another sealable bottle containing 980 mL of ultrapure water, measured by (with) measuring glass, and the pipette tip was flushed a few times. Then, 500 mL of this solution was taken using a measuring glass and poured into a 10 L bucket. Then, 0.13 g of CH3COONa and 0.22 g of NaHCO$_3$ were dissolved into 500 mL of ultrapure water and poured into the bucket. Finally, 9000 mL of ultrapure water was added using 500 mL and 2000 mL measuring glasses.

1000 mL of so prepared solution was taken using a measuring glass and poured into 1 L beakers that were combined with Kemira flocculator as described above, and then used in the coagulation and flocculation experiments. pH was adjusted to 7.1-7.6 in the experiments.

The results of the experiments are shown in Table 6 and Table 7.

TABLE 6

The used chemicals, dosages, and results in Matrix 1.

| Treatment, chemical | Chemical dose, mmol Me/L | Counts (all) | Counts (MP gate) | Microplastics removal % | Disturbing counts (MP gate) | Disturbing counts (MP gate)/Counts (MP gate), % |
|---|---|---|---|---|---|---|
| Zero | 0 | 187670 | 145787 | 0% | 0 | 0.0% |
| Ferric chloride | 0.02 | 266870 | 89530 | 39% | 155 | 0.2% |
| Ferric chloride | 0.04 | 248145 | 64110 | 56% | 285 | 0.4% |
| Ferric chloride | 0.07 | 264373 | 11967 | 92% | 35 | 0.3% |

TABLE 6-continued

The used chemicals, dosages, and results in Matrix 1.

| Treatment, chemical | Chemical dose, mmol Me/L | Counts (all) | Counts (MP gate) | Microplastics removal % | Disturbing counts (MP gate) | Disturbing counts (MP gate)/Counts (MP gate), % |
|---|---|---|---|---|---|---|
| Ferric chloride | 0.25 | 122550 | 3065 | 98% | 35 | 1.1% |
| Ferric chloride | 0.37 | 107240 | 5945 | 96% | 20 | 0.3% |
| Polyaluminium chloride | 0.02 | 88220 | 37105 | 75% | 90 | 0.2% |
| Polyaluminium chloride | 0.05 | 57810 | 26525 | 82% | 230 | 0.9% |
| Polyaluminium chloride | 0.08 | 69420 | 8193 | 94% | 110 | 1.3% |
| Polyaluminium chloride | 0.25 | 48435 | 5135 | 96% | 125 | 2.4% |
| Polyaluminium chloride | 0.37 | 62040 | 4790 | 97% | 35 | 0.7% |

TABLE 7

The used chemical, dosages and results in Matrix 1.

| Treatment, chemical | Chemical dose, mg/L | Counts (all) | Counts (MP gate) | Microplastics removal % | Disturbing counts (MP gate) | Disturbing counts (MP gate)/Counts (MP gate), % |
|---|---|---|---|---|---|---|
| Zero | 0 | 187670 | 145787 | 0% | 0 | 0.00% |
| C-577 | 0.25 | 152733 | 90700 | 38% | 60 | 0.07% |
| C-577 | 0.5 | 133515 | 86060 | 41% | 75 | 0.09% |
| C-577 | 1 | 158000 | 111015 | 24% | 515 | 0.46% |
| C-577 | 2 | 136890 | 110295 | 24% | 50 | 0.05% |
| C-577 | 10 | 124035 | 101410 | 30% | 15 | 0.01% |
| C-577 | 20 | 130975 | 106690 | 27% | 385 | 0.36% | b) Matrix 2

Preparation of Matrix 2: MP1 was poured into a small beaker. From this beaker, 495 µL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, 20 mL of this solution was pipetted into another sealable bottle containing 980 mL of ultrapure water, measured by (with) measuring glass, and the pipette tip was flushed a few times. Then, 500 mL of this solution was taken using a measuring glass and poured into a 10 L bucket. Then, 0.13 g of CH3COONa and 0.22 g of NaHCO$_3$ were dissolved into 500 mL of ultrapure water and poured into the bucket. Humic acids (HA) were added to the solution. First, 0.3314 g of HA were weighed into a beaker, 1.6 mL of 1 mol/L NaOH and approximately 300 mL of ultrapure water were added. The solution was mixed using magnetic stirrer. After mixing well, this HA solution was poured into a volumetric flask and diluted to 1000 mL and added to the 10 L bucket. Finally, 8000 mL of ultrapure water was added to the bucket using 2000 ml measuring glasses.

1000 mL of so prepared solution was taken using a measuring glass and poured into 1 L beakers that were combined with Kemira flocculator as described above, and then used in the coagulation and flocculation experiments. pH was adjusted to 7.0-7.6 in the experiments. The results of the experiments are shown in Table 8 and Table 9.

TABLE 8

The used chemicals, dosages, and results in Matrix 2.

| Treatment, chemical | Chemical dose, mmol Me/L | Counts (all) | Counts (MP gate) | Microplastics removal % | Disturbing counts (MP gate) | Disturbing counts (MP gate)/Counts (MP gate), % |
|---|---|---|---|---|---|---|
| Zero | 0 | 1527870 | 142990 | 0% | 1400 | 1% |
| Ferric chloride | 0.04 | 1572640 | 138440 | 3% | 1170 | 1% |
| Ferric chloride | 0.2 | 1788810 | 144480 | −1% | 1070 | 1% |
| Ferric chloride | 0.4 | 1593140 | 141970 | 1% | 1030 | 1% |
| Ferric chloride | 0.6 | 1589195 | 141285 | 1% | 1020 | 1% |
| Ferric chloride | 0.9 | 5848687 | 92567 | 35% | 130 | 0% |
| Ferric chloride | 1.1 | 1988950 | 36110 | 75% | 120 | 0% |
| Ferric chloride | 1.2 | 1153777 | 33970 | 76% | 380 | 1% |

TABLE 8-continued

The used chemicals, dosages, and results in Matrix 2.

| Treatment, chemical | Chemical dose, mmol Me/L | Counts (all) | Counts (MP gate) | Microplastics removal % | Disturbing counts (MP gate) | Disturbing counts (MP gate)/Counts (MP gate), % |
|---|---|---|---|---|---|---|
| Ferric chloride | 1.4 | 883530 | 29710 | 79% | 60 | 0% |
| Polyaluminium chloride | 0.03 | 1591940 | 137440 | 4% | — | |
| Polyaluminium chloride | 0.2 | 1627770 | 143820 | −1% | — | |
| Polyaluminium chloride | 0.4 | 1441820 | 142880 | 0% | 60 | 0% |
| Polyaluminium chloride | 0.6 | 1211113 | 58373 | 59% | 445 | 1% |
| Polyaluminium chloride | 0.8 | 721935 | 37575 | 74% | 360 | 1% |
| Polyaluminium chloride | 0.9 | 234570 | 2770 | 98% | 1160 | 42% |
| Polyaluminium chloride | 1.1 | 264520 | 5000 | 97% | 800 | 16% |
| Polyaluminium chloride | 1.2 | 166233 | 2530 | 98% | — | |
| Polyaluminium chloride | 1.4 | 164140 | 2700 | 98% | 3400 | 126% |

TABLE 9

The used chemical, dosages, and results in Matrix 2.

| Treatment, chemical | Chemical dose, mg/L | Counts (all) | Counts (MP gate) | Microplastics removal % | Disturbing counts (MP gate) | Disturbing counts (MP gate)/Counts (MP gate), % |
|---|---|---|---|---|---|---|
| Zero | 0 | 1527870 | 142990 | 0% | 1400 | 1.0% |
| C-577 | 43 | 1538130 | 147520 | −3% | — | |
| C-577 | 862 | 1505230 | 140340 | 2% | — | |
| C-577 | 1720 | 1609750 | 141410 | 1% | — | |
| C-577 | 2100 | 1621600 | 138070 | 3% | — | |
| C-577 | 2500 | 2864380 | 36590 | 74% | — | |
| C-577 | 3000 | 542400 | 19110 | 87% | 1100 | 5.8% |
| C-577 | 3050 | 603460 | 15020 | 89% | — | |
| C-577 | 3100 | 507070 | 20940 | 85% | — | |
| C-577 | 3150 | 732320 | 19830 | 86% | — | |
| C-577 | 3200 | 781240 | 23200 | 84% | 330 | 1.4% | c) Microplastics Containing Secondary Wastewater Effluent

Preparation of the first batch of microplastics containing secondary wastewater effluent, Matrix 3a:

MP1 was poured into a small beaker. From this beaker, 495 μL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and a stirring that allowed the overall solution to mix homogeneously with a small vortex was turned on. While stirring, 20 mL of this solution was pipetted into another sealable bottle containing 980 mL of ultrapure water, measured by (with) measuring glass, and the pipette tip was flushed a few times. Then, 500 mL of this solution was taken using a measuring glass and poured into a 10 L bucket. Then, 9500 mL of secondary wastewater treatment plant effluent was taken using a measuring glass and was added to the bucket.

1000 mL of so prepared solution was taken using a measuring glass and poured into 1 L beakers that were combined with Kemira flocculator as described above, and then used in the coagulation and flocculation experiments. The pH was adjusted to 7.0-7.5 in the experiments.

The used chemicals, dosages and results of the experiments are shown in Table 10.

The used effluent properties were as follows:

COD=28.5-39.7 mg/L

Suspended solids=0.003-0.008 g/L

P-tot=0.189 mg/L

Dissolved PO4-P (0.45 μm filtrate)=<0.05 mg/L

UV absorbance (0.45 μm filtrate)=0.160

Color=23 PtCo

Turbidity=3.66-4.89 NTU

TABLE 10

The used chemicals, dosages, and results in Matrix 3a.

| Treatment, chemical | Chemical dose, mmol Me/L | Counts (all) | Counts (MP gate) | Microplastics removal % | Disturbing counts (MP gate) | Disturbing counts (MP gate)/Counts (MP gate), % |
|---|---|---|---|---|---|---|
| Zero | 0 | 804278 | 108430 | 0% | 70 | 0.1% |
| Ferric chloride | 0.03 | 950490 | 92310 | 15% | 260 | 0.3% |
| Ferric chloride | 0.07 | 999380 | 80740 | 26% | 25 | 0.0% |
| Ferric chloride | 0.16 | 760470 | 43417 | 60% | 10 | 0.0% |
| Ferric chloride | 0.25 | 693075 | 18895 | 83% | 35 | 0.2% |
| Ferric chloride | 0.37 | 566470 | 3950 | 96% | 20 | 0.5% |
| Ferric chloride | 0.88 | 301170 | 590 | 99% | 0 | 0.0% |
| Ferric chloride | 1.23 | 347230 | 120 | 100% | 10 | 8.3% |
| Polyaluminium chloride | 0.03 | 788790 | 110860 | −2% | 40 | 0.0% |
| Polyaluminium chloride | 0.08 | 562695 | 47830 | 56% | 100 | 0.2% |
| Polyaluminium chloride | 0.16 | 447877 | 10387 | 90% | 20 | 0.2% |
| Polyaluminium chloride | 0.25 | 414150 | 6220 | 94% | 10 | 0.2% |
| Polyaluminium chloride | 0.37 | 336520 | 4240 | 96% | — | — |
| Polyaluminium chloride | 0.62 | 263960 | 2780 | 97% | 270 | 9.7% |
| Polyaluminium chloride | 0.88 | 233270 | 2930 | 97% | — | — |
| Polyaluminium chloride | 1.05 | 187200 | 2290 | 98% | — | — |
| Polyaluminium chloride | 1.23 | 178340 | 1990 | 98% | 140 | 7.0% |

Preparation of a second batch of microplastics containing secondary wastewater effluent, Matrix 3b:

MP1 was poured into a small beaker. From this beaker, 495 µL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and a stirring that allowed the overall solution to mix homogeneously with a small vortex was turned on. While stirring, 20 mL of this solution was pipetted into another sealable bottle containing 980 mL of ultrapure water, measured by (with) measuring glass, and the pipette tip was flushed a few times. Then, 500 mL of this solution was taken using a measuring glass and poured into a 10 L bucket. Then, 9500 mL of secondary wastewater treatment plant effluent was taken using a measuring glass and was added to the bucket.

1000 mL of solution prepared in such a way was taken using a measuring glass and poured into 1 L beakers that were combined with Kemira flocculator as described above, and then used in the coagulation and flocculation experiments. The pH was adjusted to 6.6-6.9 in the experiments.

The used chemicals, dosages and results are shown in Table 11.

TABLE 11

The used chemicals, dosages, and results in Matrix 3b.

| Treatment, chemical | Chemical dose, mmol Me/L | pH of experiment | Counts (all) | Counts (MP gate) | Removal % | Disturbing counts (MP gate) | Disturbing counts (MP gate)/Counts (MP gate), % |
|---|---|---|---|---|---|---|---|
| Zero | 0 | 6.6 | 1862900 | 109370 | 0% | — | —1 |
| Ferric sulphate | 0.07 | 6.8 | 1433880 | 80240 | 27% | — | — |
| Ferric sulphate | 0.16 | 6.7 | 879880 | 15900 | 85% | 70 | 0.4% |
| Ferric sulphate | 0.37 | 6.6 | 586210 | 870 | 99% | — | — |
| Ferric sulphate | 0.88 | 6.9 | 448300 | 250 | 100% | — | — |

Preparation of the third batch of microplastics containing secondary wastewater effluent, Matrix 3c:

1000 mL of the secondary wastewater effluent was measured using measuring glass and poured to 1 L beaker. MP3 was poured into a small beaker. From this beaker, 259 μL of the product was pipetted into the 1 L beaker containing effluent, and the pipette tip was flushed few times. This was repeated for each sample, which were then combined with the Kemira flocculator as described above, and then used in the coagulation and flocculation experiments. The pH was adjusted to 6.6-6.9 in the experiments.

The used chemicals, dosages and results are shown in Table 12.

TABLE 12

The used chemicals, dosages, and results in Matrix 3c.

| Treatment, chemical | Chemical dose, mmol Me/L | pH of experiment | Counts (all) | Counts (MP gate) | Removal % |
|---|---|---|---|---|---|
| Zero | 0 | 6.6 | 1669830 | 44800 | 0% |
| Polyaluminium chloride | 0.08 | 6.7 | 509160 | 4640 | 90% |
| Polyaluminium chloride | 0.16 | 6.7 | 230810 | 2530 | 94% |
| Polyaluminium chloride | 0.25 | 6.9 | 263910 | 8350 | 81% |
| Polyaluminium chloride | 0.37 | 6.8 | 170220 | 4180 | 91% |

Preparation of the fourth batch of microplastics containing secondary wastewater effluent, Matrix 3d:

500 mL of ultrapure water (Millipore, Milli-Q, Q-POD) and 9500 mL of secondary wastewater treatment plant effluent were combined in a 10 L bucket. The solution was mixed, and approximately 100 mL of it was taken into a small beaker. MP5 was poured into a small beaker from which 3901 μL of the product was pipetted into the beaker containing the effluent-ultrapure water solution, and the pipette tip was flushed a few times. This mixture was then poured to a 1 L measuring glass, which was then filled with the effluent-ultrapure water solution and emptied to another 10 L bucket. 4100 mL of effluent-ultrapure solution was added, and the solution was mixed. 1000 mL of a solution prepared in such a way was taken using a measuring glass and poured into 1 L beakers which were combined with the Kemira flocculator as described above, and then used in the coagulation and flocculation experiments. pH was adjusted to 6.6-7.0 in the experiments.

The used chemicals, dosages and results are shown in Table 13.

TABLE 13

The used chemicals, dosages, and results in Matrix 3d.

| Treatment, chemical | Chemical dose, mmol Me/L | pH of experiment | Counts (all) | Counts (MP gate) | Removal % |
|---|---|---|---|---|---|
| Zero | 0 | 6.8 | 1168070 | 6950 | 0% |
| Ferric chloride | 0.07 | 6.9 | 1164740 | 1110 | 84% |
| Ferric chloride | 0.16 | 6.8 | 632210 | 130 | 98% |
| Ferric chloride | 0.37 | 6.6 | 448350 | 50 | 99% |
| Ferric chloride | 0.88 | 7.0 | 346070 | 50 | 99% |

Other factors influencing the needed iron and aluminium dose:

The concentration of dissolved phosphorus that is bound in the phosphate (PO4-P) was low in the used secondary wastewater effluent. However, it can be higher in other waters that are treated and from which the microplastics are removed. The concentration of PO4-P influences the iron or aluminium dose. The higher the PO4-P concentration, the more iron or aluminium is consumed in removing the dissolved PO4-P from water. The typical iron or aluminium amount needed to remove PO4-P is 1.5 moles of iron or aluminium per mole of PO4-P (Me/P mol/mol). The potential influence of PO4-P of water from which the microplastics are removed on the required additional iron or aluminium dose, is shown in Table 14.

TABLE 14

Potential influence of $PO_4$-P of water on the required additional iron or aluminium dose that is needed on top of the dose needed to remove microplastics.

| Me/P, mol/mol | $PO_4$-P, mgP/L | Me requirement, mmol Me/L |
|---|---|---|
| 1.5 | 0.5 | 0.024 |
| 1.5 | 2 | 0.097 |
| 1.5 | 10 | 0.484 |

Also, the carbon and suspended solids content in the effluent consume iron and aluminium, and the higher these are, the higher dosage of iron or aluminium is needed.

Preparation of the first batch of microplastics containing secondary wastewater effluent, Matrix 3e:

MP1 was poured into a small beaker. From this beaker, 495 μL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, 20 mL of this solution was pipetted into a small beaker containing ultrapure water, and the pipette tip was flushed few times. This solution was then poured into a 1-L volumetric flask that was filled to the mark with ultrapure water. Then, 500 mL of this solution was taken using a measuring glass and poured into a 10-L bucket. Then, 9500 mL of secondary wastewater treatment plant effluent was taken using a measuring glass and was added to the bucket.

1000 mL of a solution prepared in such a way was taken using a measuring glass and poured into 1-L beakers which were combined with the Kemira flocculator as described above, and then used in the coagulation and flocculation experiments. pH was adjusted to 7.2-7.3 in the experiments. The used chemicals, dosages and results of the experiments are shown in Table 15.

TABLE 15

The used chemicals, dosages, and results in Matrix 3e.

| Treatment, chemical | Chemical dose, mg/L | Counts (all) | Counts (MP gate) | Microplastics removal % | Disturbing counts (MP gate) | Disturbing counts (MP gate)/Counts (MP gate), % |
|---|---|---|---|---|---|---|
| Zero | 0 | 1623810 | 83740 | 0% | NA | NA |
| Superfloc C-577 | 34.8 | 496990 | 31660 | 62% | 910 | 3% |
| Superfloc C-577 | 37.7 | 638180 | 38400 | 54% | 890 | 2% |
| Superfloc C-577 | 40.6 | 956770 | 47090 | 44% | 890 | 2% |
| Superfloc C-577 | 46.4 | 1746620 | 59820 | 29% | NA | NA | d) Lake Water

Preparation of microplastics containing lake water (Matrix 4):

MP1 was poured into a small beaker. From this beaker, 495 μL of the product was pipetted into a small beaker containing ultrapure water, and the pipette tip was flushed a few times. Then, this solution was poured into a 50-mL volumetric flask that was filled to the mark with ultrapure water (Millipore, Milli-Q, Q-POD). This solution was then poured into a sealable bottle to allow for pipetting under magnetic stirrer (during magnetic stirring). A magnet was added into the bottle, the bottle was placed on the magnetic stirrer and such a stirring was turned on that allowed the overall solution to mix homogeneously with a small vortex. While stirring, 20 mL of this solution was pipetted into another sealable bottle containing 980 mL of ultrapure water, measured by (with) measuring glass, and the pipette tip was flushed a few times. Then, 500 mL of this solution was taken using a measuring glass and poured into a 10 L bucket. Then, 9500 mL of lake water was taken using a measuring glass and was added to the bucket.

1000 mL of a solution prepared in such a way was taken using a measuring glass and poured into 1 L beakers which were combined with the Kemira flocculator as described above, and then used in the coagulation and flocculation experiments. pH was adjusted to 6.6-7.2 in the experiments.

The used chemicals, dosages and results are shown in Table 16.

TABLE 16

The used chemicals, dosages, and results in Matrix 4.

| Treatment, chemical | Chemical dose, mmol Me/L | pH in experiment | Counts (all) | Counts (MP gate) | Removal % |
|---|---|---|---|---|---|
| Zero | 0 | 7.2 | 674135 | 140325 | 0% |
| Polyaluminium chloride | 0.11 | 6.9 | 159855 | 5520 | 96% |
| Polyaluminium chloride | 0.14 | 6.8 | 122245 | 6620 | 95% |
| Polyaluminium chloride | 0.17 | 6.7 | 98875 | 5965 | 96% |
| Polyaluminium chloride | 0.20 | 6.6 | 92690 | 5610 | 96% |

Example 4. Removal of Microplastic Fibers from Water Matrix by Coagulation/Flocculation Using Ferric Chloride For preparing polyester (PES) fibers, fleece fabric was purchased from a fabric store, and the material was verified with FTIR spectroscopy. Fibers were prepared by brushing with a hard metal brush. The use of brush made the fibers pack tightly, which had adverse effect on dispersing fibers into water. Very intense packing was minimized by using very short strokes and removing fibers from the brush more often.

1.00 g of this way prepared fibers were mixed to total of 1000 mL of ultrapure water in a following way: the fiber amount was divided into two beakers with 450 mL of ultrapure water in each and dispersed using fast mixer (fast mixing). Then the beakers were combined, 100 mL of ultrapure water was added, and the solution was let to settle for approximately half an hour. This was done to exclude the fibers that had settled within this time frame, and to include mainly fibers that would not settle without chemical treatment. After the settling, the remaining fiber solution was pipetted, and several such batches were combined to one bucket. The settled and excluded fibers were weighed, and the dispersed fiber amount according to this was 0.0316 g. Then, 1.30 g CH3COONa and 2.20 g $NaHCO_3$ were added to the solution, that was then diluted to a volume of ten litres. This resulted in a fiber sample solution with a fiber concentration of 0.003 g/L. Then, the solution was homogenized mixing it slowly, and four 1 L samples were taken with a plastic jar and measuring glass. A coagulation/flocculation experiment was performed for these samples with FeCl3.

Figure 5:
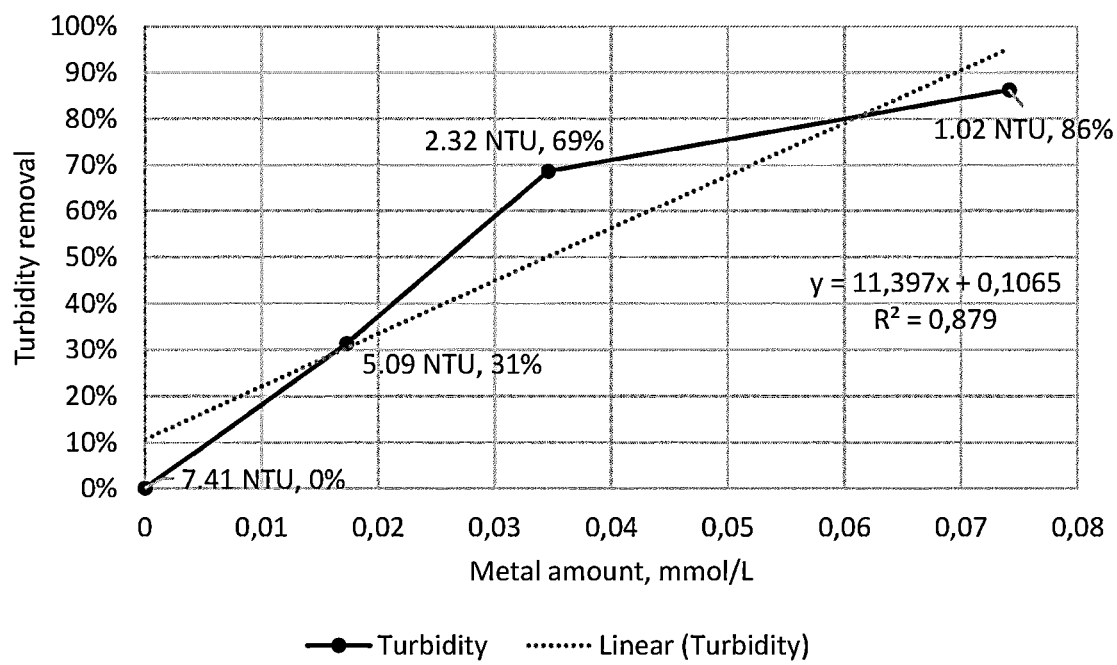
FIG. 5 shows turbidity removal of fiber samples after treatment with ferric chloride. Absolute turbidity with removal percentage next to each sample point.

The original turbidity in the sample solution was 12.2 NTU, that decreased to 7.4 NTU with the treatment without chemical. The turbidity was further decreased with increasing chemical dose (dosage) finally reaching 1.0 NTU. This indicates a 86% fiber removal when compared to the sample treated without chemical. The turbidity removal is shown in Table 17 and in FIG. 5.

TABLE 17

Used coagulant dosages and the treatment results in Matrix 1.

| Treatment | Chemical dose, mmol Me/L | Turbidity (NTU) | Microplastics removal % |
|---|---|---|---|
| Zero | 0 | 7.41 | 0% |
| Polyaluminium chloride | 0.017 | 5.09 | 31% |
| Polyaluminium chloride | 0.035 | 2.32 | 69% |
| Polyaluminium chloride | 0.074 | 1.02 | 86% |

The invention claimed is:

1. A method of selecting a suitable chemistry for removal of microplastics in a liquid matrix, said method comprising the steps of:
   a. providing a predetermined volume of a liquid matrix,
   b. adding a preset amount of a chemical system comprising at least one coagulant and/or flocculant to the liquid matrix of step a), and allowing the added chemical system to interact to form flocs and/or aggregates containing any microplastic particles, if present in the liquid matrix,
   c. removing flocs and/or aggregates containing any microplastic particles of the liquid matrix in a separation step to form a clarified liquid matrix,
   d. measuring fluorescence intensity and light scattering intensity of any particles in a sample volume of clarified liquid matrix by an optical detection method comprising,
      d'. gathering and combining the scattering intensity data and the fluorescence intensity data of the particles,
      d". identifying particle populations of the measured data representing microplastic particles populations based on predetermined identification data, and
      d'". determining the number of microplastic particles of the microplastic particles populations,
   e. assessing the efficiency of microplastics removal based on:
   the number of microplastic particles in the sample volume used in step d),
   or
   the number of microplastic particles in the sample volume used in step d) compared to a known number of microplastic particles, if used, added to the liquid matrix in step a);
   and wherein steps a) to e) are repeated with other chemical systems than said at least one chemical system, and further comprising the steps of:
   f. comparing the efficiency of microplastics removal of all chemical systems tested, and
   g. based on these results selecting as the chemistry for removal of microplastics in a liquid matrix the chemical system which provides for the most efficient removal of microplastic particles.

2. The method according to claim 1, further comprising the step of:
   a'. introducing to the predetermined volume a known number of microplastic particles, performed after step a and before step b.

3. The method according to claim 1, further comprising the step of:
   e'. performing the same separation step as in c), and performing a measurement in accordance with step d), or d) to d'), or d) to d"), or d to d'").

4. The method according to claim 1, wherein the liquid matrix is mixed during at least one of step a'), and b).

5. The method according to claim 1, wherein the liquid matrix is a water matrix.

6. The method of claim 1, wherein the removal of flocs and/or aggregates of step c) is performed by a separation method selected from sedimentation, filtration, flotation, froth flotation, dissolved air flotation, or any combination thereof; or by sedimentation.

7. The method of claim 1, wherein the predefined identification data comprises at least one of:
   comparing with reference data of scattering intensity and the fluorescence intensity of said known microplastic particles, and identifying an area of a plotted graph of the scattering intensity and the fluorescence intensity representing the microplastic particles populations; or
   comparing the scattering intensity and the fluorescence intensity data of microplastic particles of the liquid matrix in step a) and optionally step a') measured by taking a sample of the liquid matrix in step a) and optionally a sample of the liquid matrix in step a') and performing measurements in accordance with steps d) and optionally d'); or
   comparing the scattering intensity and the fluorescence intensity data of microplastic particles of a liquid matrix other than the liquid matrix of step a), and another sample of said other liquid matrix, being than the liquid matrix of step a) and introducing thereto a predetermined amount a known number of microplastics, by taking samples of the liquid matrices, doped and undoped with microplastic particles, and performing measurements in accordance with steps d) and optionally d').

8. The method of claim 1, wherein the flocculant is a polymer.

9. The method according to claim 8, wherein the polymer comprises at least one of:
  (i) an anionic polymer comprising at least one monomer selected from acrylamide (AMD), (2-acrylamido-2-methyl-1-propanesulfonic acid) (AMPS) and acrylic acid (AA) and any combination thereof;
  (ii) a cationic polymer comprising at least one monomer selected from cationic polyacrylamide, poly (diallyldimethylammonium chloride), polyamine, melamine-formaldehyde resin, polydicyandiamide, and any combination thereof;
  (iii) a nonionic polymer comprising acrylamide (AMD) monomer;
  (iv) a polysaccharides selected from cellulose, starch, chitin and chitosan compounds, and any combination thereof; and
  (v) a polyphenolics selected from tannins, lignin, and any combination thereof.

10. The method of claim 1, wherein the coagulant comprises an inorganic coagulant.

11. The method of claim 1, wherein the coagulant is admixed in an amount which provides for a concentration of metal from the coagulant in the microplastic containing liquid matrix of 0.01-1.5 mmol/l, 0.01-1.2 mmol/l, 0.05-1 mmol/l, 0.1-0.9 mmol/l, 0.1-0.8 mmol/l, 0.2-0.6 mmol/l, or 0.3-0.5 mmol/l.

12. The method of claim 1, wherein the microplastics comprise one or more of polyethylene, polypropylene, polyvinylchloride, polyurethane, polystyrene, polyamide, polyester, acrylonitrile butadiene styrene, polytetrafluoroethylene, cellulose acetate, polycarbonate, polymethylmethacrylate, polyethylene terephthalate, polyvinylidene chloride, phenol formaldehyde, or melamine formaldehyde polymers, and derivatives thereof.

13. The method of claim 1, wherein the size of the microplastic particles is 0.1-100 µm, 1-100 µm, 5-50 µm, or 6-50 µm.

14. The method of claim 1, wherein the microplastic containing water or treated water, prior to the optical measurement is admixed with a fluorescent dye that results in selective staining of the microplastics.

15. The method of claim 1, wherein the optical measurement includes the use of flow cytometry.

16. The method of claim 5, wherein the water matrix is selected from microplastic containing raw water, drinking water, storm water, water originating from melted snow, surface water, effluent of industrial wastewater treatment plants, effluent of municipal wastewater treatment plants, or industrial process water.

17. The method of claim 8, wherein the flocculant is a polymer selected from the group anionic polymers, cationic polymers, nonionic polymers, amphoteric polymers, polysaccharides, polyphenolic compounds, and any combination thereof.

18. The method of claim 10, wherein the coagulant is selected from (i) an inorganic coagulant comprising iron containing salts, aluminium containing salts, magnesium containing salts, or any derivative thereof, (ii) chlorides, sulphates, chlorosulphates, chlorohydrates, silicates, nitrates, and any derivative thereof; (iii) aluminium sulfate, polyaluminium sulfate, aluminium chloride, polyaluminium chloride, polyaluminium chlorosulfate, polyaluminium hydroxychlorosulfate, aluminium chlorohydrate, sodium aluminate, ferric sulfate, polyferric sulfate, ferric chloride, ferric chlorosulphate, polyferric chloride, ferrous sulfate, ferrous chlorosulphate, ferrous chloride, aluminium triformate, polyaluminium formate, polyaluminium nitrate, polyaluminium silicate, magnesium chloride, and derivatives thereof, and (iv) any combination of one, two or all three of (i), (ii) and (iii).

19. The method of claim 14, wherein the fluorescent dye is a lipophilic stain.

\* \* \* \* \*